(12) United States Patent
Losquadro

(10) Patent No.: US 12,426,979 B2
(45) Date of Patent: Sep. 30, 2025

(54) FORESKIN RECONSTRUCTION AND RESTORATION METHODS AND DEVICES

(71) Applicant: Anthony Losquadro, Glen Head, NY (US)

(72) Inventor: Anthony Losquadro, Glen Head, NY (US)

( * ) Notice: Subject to any disclaimer, the term of this patent is extended or adjusted under 35 U.S.C. 154(b) by 707 days.

(21) Appl. No.: 17/664,917

(22) Filed: May 25, 2022

(65) Prior Publication Data
US 2023/0380924 A1     Nov. 30, 2023

(51) Int. Cl.
*A61B 90/00* (2016.01)

(52) U.S. Cl.
CPC .................. *A61B 90/02* (2016.02)

(58) Field of Classification Search
CPC .............................. A61B 90/02; A61M 29/00
USPC ........................................ 606/190, 192, 198
See application file for complete search history.

(56) References Cited

U.S. PATENT DOCUMENTS

| | | | |
|---|---|---|---|
| 6,579,227 B2 | 6/2003 | Haughey | |
| 2005/0027269 A1 | 2/2005 | Brown | |
| 2005/0090708 A1* | 4/2005 | Low | A61B 17/326 |
| | | | 600/38 |
| 2011/0166414 A1 | 7/2011 | Watts | |
| 2023/0149111 A1* | 5/2023 | Lomholt | A61B 90/02 |
| | | | 600/38 |

FOREIGN PATENT DOCUMENTS

WO      2015/128365 A1      9/2015

OTHER PUBLICATIONS

"Foreskin Restoration Cat II Q Device", 2 pages, site visited Jul. 16, 2025, https://calstrelcher.com/.
"Hyperrestore Products", 2 pages, site visited Jul. 16, 2025, http://hyperrestore.com/products/.

* cited by examiner

*Primary Examiner* — Samuel G Gilbert
(74) *Attorney, Agent, or Firm* — Collard & Roe, P.C.

(57) ABSTRACT

Methods and devices for foreskin restoration and reconstruction are provided that capture folded skin and allow the user to blow air pressure in the fold of skin, inflating the skin and placing it under tension to induce skin growth using devices that are comfortable and tolerable. The devices include an outer gripper, an inner cone, a metal core, an integrated check valve, an oral inflation tube connected to an air input, and a split ring weight attachment point, which together hold shaft skin without slippage and maintain air pressure and tension the skin, to provide partial to full foreskin restoration and reconstruction.

10 Claims, 5 Drawing Sheets

FORESKIN RECONSTRUCTION AND RESTORATION METHODS AND DEVICES

FIELD OF THE INVENTION

The invention relates to methods and devices used for foreskin restoration and reconstruction.

BACKGROUND OF THE INVENTION

The act of surgical foreskin removal, whether partly or in its entirety, is known as circumcision. Circumcision has been performed for millennia mainly for religious, tribal, or cultural reasons. In the United States, it is one of the most commonly performed surgical procedures, although it is done to a much lesser extent around the world. The procedure is surrounded by controversy, further exacerbated by the fact that it is usually done on individuals below their age of consent.

Currently, the medical establishment in the United States promotes circumcision as a medical intervention for children, although the practice is simultaneously opposed by many international medical experts. The foreskin, or prepuce, has been considered by some to be an unnecessary appendage and unrelated to sexual function. Yet, others consider it to have several necessary functions, from which sexual and immunological functions seem the most prominent. Currently, concerns are being raised regarding circumcision's widespread practice and its implications later in life. These conflicting considerations have caused some of those who were circumcised as children, and others, to seek a means to restore their genitals to the extent possible. For example, newfound interest into the subject of foreskin reconstruction was illustrated in a recent study that explored the motivations and self-taken actions of men seeking foreskin reconstruction. (Ozer M, Timmermans F. "An insight into circumcised men seeking foreskin reconstruction: a prospective cohort study." Int J Impot Res. 2020; 32:641). Reasons for seeking foreskin restoration can include returning a body to its natural form, improved sexual function, improved sensitivity, and to reduce scarring or disfigurement (Shteyngart, Gary 2021 "A Botched Circumcision and Its Aftermath", The New Yorker Oct. 4, 2021).

It would be advantageous to provide new methods and devices for foreskin restoration and reconstruction that efficiently initiate the process of skin growth during foreskin restoration.

It also would be advantageous to provide new methods and devices that apply mechanotransduction through which skin cells sense and respond to tension.

It also would be advantageous to provide new methods and devices for foreskin restoration and reconstruction that are comfortable and tolerable for the user.

It also would be advantageous to provide new methods and devices for foreskin restoration and reconstruction that hold shaft skin comfortably and without slippage while maintaining air pressure.

It also would be advantageous to provide new methods and devices for foreskin restoration and reconstruction to which one can easily add weights that pull on the shaft skin combined with air pressure to depress the glans and expand the shaft skin so as to initiate mechanotransduction and cellular mitosis.

It also would be advantageous to provide new methods and devices for foreskin restoration and reconstruction that obtain partial to full foreskin restoration and/or that provide a partial to full facsimile foreskin.

Methods and devices for safe and efficacious foreskin reconstruction are thus needed. Such methods and devices would preferably be efficient, inexpensive, non-surgical, tolerable and cause less (or no) pain or discomfort.

SUMMARY OF THE INVENTION

Embodiments of this invention concern new methods and devices for restoration and reconstruction of penis foreskin. Certain preferred embodiments of this invention comprise a method for penis foreskin reconstruction that comprises (a) placing a device on the penis of the user using an outer gripper of the device, the device comprising the outer gripper, an inner cone, a metal core (which in certain embodiments comprises a stainless-steel core), an integrated check valve, an oral inflation tube connected to an air input (e.g., a reversed air input), and a split ring weight attachment point, the outer gripper forming an air-tight seal around the penis; (b) applying air pressure to penile shaft skin so that it is held by the inner cone and the outer gripper comfortably and without slipping; and (c) adding additional tension to the device by hanging weights on the split ring weight attachment point.

Particularly preferred embodiments of this invention comprise a method for penis foreskin restoration and reconstruction that comprises (a) placing a device over a penis shaft using one or more finger grab tabs connected to an outer gripper; (b) inflating penis shaft skin and holding it firmly between an inner cone and an outer gripper comprising the use of (i) a metal core connected to an integrated check valve and reversed air input that has an oral inflation tube connected to it to accept the air that is blown into it; (ii) each of the inner cone and the outer gripper having one or more serrated gripper surfaces integrated onto it to maintain the penis shaft skin in place; and (iii) the outer gripper having one or more gripper tension rings integrated onto it to prevent excessive expansion of the outer gripper during the inflating; (c) maintaining air pressure against the penis shaft skin comprising the use of (i) an interlock seal connected to the inner cone; (ii) an internal taper lock connected to a metal core and the inner cone; (iii) the one or more serrated gripper surfaces; (iv) a compression ferrule that holds the inner cone on the metal core; (v) an integrated check valve; and (vi) the one or more gripper tension rings integrated onto the outer gripper; and (d) applying tension to penile shaft skin by using a split ring weight attachment point to add weights to the device. In certain embodiments, the outer gripper, on its inner surface, may have a plurality of circulatory relief grooves to reduce or prevent ischemia. In certain embodiments, the inner cone, on its outer surface, may have a skin fold relief groove to reduce or prevent pinching and ischemia of the leading edge of skin.

Certain preferred embodiments of this invention comprise a device for penis foreskin restoration and reconstruction that comprises (a) an outer gripper and outer gripper tabs for gripping or grasping with the hand to place the device on the penis of the user, the outer gripper covering an inner cone, the outer gripper also forming an air-tight seal around the penis; (b) the inner cone that along with the outer gripper holds penis shaft skin comfortably and without slipping; (c) an oral inflation tube for blowing air into the device to add air pressure that is applied to the penis shaft skin to hold it in place and add tension; and (d) a split ring weight attachment point on the end of the device that is capable of accepting weights to add tension to the penis shaft skin.

Particularly preferred embodiments of this invention comprise a device for penis foreskin restoration and reconstruction that comprises (a) a metal core (which in some embodiments is comprised of a stainless-steel core); (b) a split ring weight attachment point connected to the metal core, the split ring weight attachment point for applying weights to the distal end of the device and thereby adding tension to penis shaft skin; (c) a reversed air input connected to the metal core that permits attachment of an oral inflation tube to the reversed air input; (d) the oral inflation tube connected to the reversed air input and the oral inflation tube providing a way for a user to introduce air pressure into the device to inflate penis shaft skin; (e) an interlock seal connected to an inner cone that prevents air escape from inside of the inner cone; (f) an internal taper lock connected to the metal core and the inner cone and holding them together, the internal taper lock providing an air seal; (g) one or more gripper tension rings integrated onto an outer gripper, the gripper tension rings inhibiting any excessive expansion of the outer griper thereby preventing penis shaft skin slippage and air leaks; (h) one or more finger grab tabs connected to the outer gripper to provide a gripping surface to place or remove the outer gripper over the penis shaft skin; (i) one or more serrated gripper surfaces that are circular grooves cast on both the inner cone and the outer gripper that serve to grip penis shaft skin to prevent slippage and air loss; (j) the inner cone and the outer gripper conform to the shape of the penis with a double angle taper; (k) a compression ferrule connected to the metal core and the inner cone and which locks them together and prevents air leaks; (l) a locking collar that locks the outer gripper in a position that maintains the device's grip on the penis shaft skin; (m) an integrated check valve that is connected to the metal core and that restricts air pressure to one-way flow to prevent air pressure from escaping the device; (n) the outer gripper, connected to the metal core, retains the inner cone over the penis shaft skin and makes an air-tight seal over the penis; and (o) the inner cone connected to the metal core that centers the penis in the device, whereby the penis shaft skin is placed over the exterior of the inner cone, permitting the outer gripper to hold the penis shaft skin in position. In certain embodiments, the outer gripper may have a plurality of circulatory relief grooves. In certain embodiments, the inner cone may also have a skin fold relief groove.

It is an object of certain embodiments of this invention to provide methods and devices that can efficiently initiate the process of skin growth during foreskin restoration and reconstruction.

It is an object of certain embodiments of this invention to provide methods and devices that apply mechanotransduction through which skin cells sense and respond to tension.

It is another object of certain embodiments of this invention to provide methods and devices for foreskin restoration and reconstruction that are comfortable and tolerable for the user.

It is another object of certain embodiments of this invention to hold shaft skin comfortably and without slippage while maintaining air pressure.

It is another object of certain embodiments of this invention to easily add weights that pull on the shaft skin so as to increase skin tension additively combined with air pressure.

It is another object of certain embodiments of this invention to provide methods and devices to obtain partial to full foreskin restoration and reconstruction and/or that provide a partial to full facsimile foreskin.

These and other objects are provided by certain embodiments of this invention. Certain embodiments of this invention provide methods and devices for safe and efficacious foreskin restoration and reconstruction that are efficient, inexpensive, non-surgical, tolerable and cause less (or no) pain or discomfort.

The preferred embodiments of this invention provide methods and devices that assist circumcised men with the process of foreskin restoration and reconstruction that involves placing penile skin under tension to stimulate skin growth. Over time, a partial to full facsimile foreskin can be regenerated. These methods and devices capture folded skin and allow the user to blow air pressure into this fold of skin, inflating the skin and depressing the glans penis. This places the penile skin under tension and induces skin growth using processes of mechanotransduction to stimulate mitosis or cell division.

DETAILED DESCRIPTION OF THE INVENTION

Figure 1:
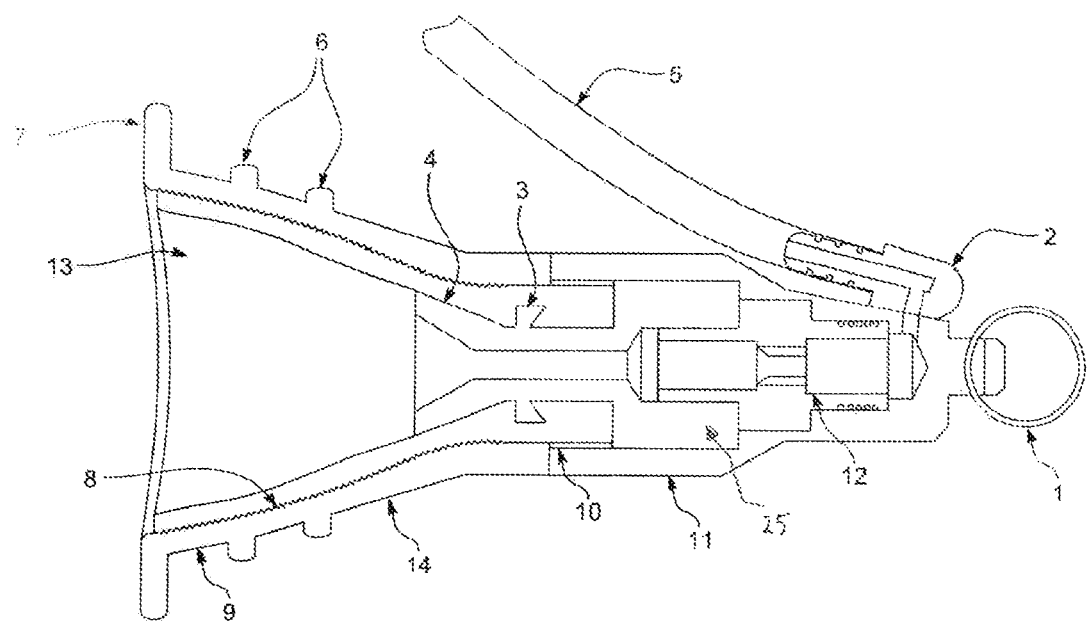
FIG. 1 is a schematic of a cross-section of a side view of an embodiment of this invention.

The embodiments of this invention apply new methods and devices to foreskin restoration and reconstruction. Reconstruction, restoration and production of a facsimile foreskin are terms that are used interchangeably herein and are intended to mean both complete and partial reconstruction, restoration and production of a facsimile foreskin. The preferred embodiments of this invention use new methods and devices that apply mechanotransduction through which skin cells sense and respond to tension (i.e., mechanical stimuli). The mechanical stimuli convert to biochemical signals that cause cellular responses. Specifically, skin cells respond to the application of tension by both growing and dividing to create more cells in a process called mitosis. Foreskin restoration methods and devices of these embodiments take advantage of mitosis to create a partial to full replacement neo-foreskin (i.e., foreskin restoration and/or a facsimile foreskin).

Certain embodiments of this invention provide foreskin restoration and reconstruction methods that place low pressure air in direct contact within a fold of penile shaft skin. The air pressure is captive inside this fold, ballooning the skin with an adjustable level of skin tension. Since fluid pressure is distributed equally to all skin surfaces, certain embodiments of the direct air methods of this invention offer high levels of efficiency and comfort.

Certain preferred embodiments of this invention provide devices that work by capturing the distal penile shaft skin to form an airtight seal within silicone rubber grippers. These devices are comprised of (i.e., they include, but are not limited to) an outer gripper, an inner cone, a metal core (that in certain embodiments comprises a stainless-steel core), an integrated check valve, a split ring weight attachment point, and an oral inflation tube.

In these preferred embodiments, the glans penis is situated against the device and medial to the grippers. The outer gripper is flipped up, and shaft skin is rolled over the inner cone. The outer gripper is then flipped down to retain the skin in place on the device and create an airtight seal. Air is orally exhaled and introduced into the device, which depresses the glans posteriorly to stretch the remnant inner foreskin. A one-way, integrated check valve prevents release of air pressure. The air pressure also balloons the held outer shaft skin, introducing radial tension to that skin. This three-dimensional stretching offers higher rates of skin expansion. A weight can also be attached to the split ring weight attachment point to increase the longitudinal stretching of the shaft skin.

In these and other preferred embodiments, as new shaft skin is created, it will tend to migrate distally to cover the glans with the appearance of a natural foreskin. Skin growth rates vary by individual but typically the user will need to wear the device for several hours a day for one to five years to obtain desired results.

Certain of the preferred devices include a metal core (which may include a stainless-steel core in some embodiments) connected to silicone rubber components. This permits only silicone rubber to come in contact with the penile skin, while the metal core and other components both provide and control air flow and connect to a mounting point for weight attachment. The components (e.g., metal and rubber) are joined in such a way as to create an airtight interlocked mechanical seal. The parts (e.g., metal parts) in some embodiments can also provide approximately five ounces of weight which further enhances skin stretching. Both the inner cone and outer gripper allow secure attachment to penile shaft skin while conforming to the glans penis and creating an airtight seal to the skin.

The preferred methods and devices of this invention utilize the user's breath exhalation via an oral inflation tube to introduce air pressure into the device and thus balloon the skin. This feature negates or reduces the need for external inflation equipment such as bellows, pumps, syringes, or squeeze bulbs.

The subject matter of this disclosure is now described with reference to the following examples. These examples are provided for the purpose of illustration only, and the subject matter is not limited to these examples, but rather encompasses all variations which are evident as a result of the teaching provided herein.

Example 1

An AIRFORCE Foreskin Restoration Device was fabricated and used in methods of this invention. The AIRFORCE Device (FIG. 1) is comprised of a Metal Core 25 (which is preferably comprised of stainless-steel), a Split Ring Weight Attachment Point 1, a Reversed Air Input 2, an Oral Inflation Tube 5, an Interlocked Seal 3, an Inner Cone 13, an Internal Taper Lock 4, Gripper Tension Rings 6, an Outer Gripper 14, Finger Grab Tabs 7, Serrated Gripper Surfaces 8, a Double Angle Taper Cone 9, a Compression Ferrule 10, a Locking Collar 11, and an Integrated Check Valve 12.

The Metal Core 25 provides attachments and connections for several other components.

The Split Ring Weight Attachment Point 1 provides a means to attach hanging weights to the device. The weights will have the effect of transmitting force through the body of the device to the skin to apply additional tension to penile shaft skin. The amount of weight can be varied as appropriate as the restoration process proceeds. It is connected to the Metal Core 25.

The Reversed Air Input 2 allows attachment of the Oral Inflation Tube 5 which provides a way of introducing low pressure air into the device which will inflate the skin fold. The reversed direction allows the Oral Inflation Tube 5 to be routed upwards on the body towards the waist while allowing the penis to naturally point downwards. This component features a barb fitting to permit attachment of the Oral Inflation Tube 5. It is connected to the Metal Core 25.

The Interlock Seal 3 prevents air escape from inside of the Inner Cone 13 around, what is in some embodiments, a silicone rubber-stainless-steel interface. Should the device lose air pressure from leaks, the foreskin restoration process would be less effective or cease, and the user would have to constantly re-inflate the device. The Interlock Seal 13 prevents air loss from this area.

The Internal Taper Lock 4 connects the Metal Core 25 to the silicone rubber of the Inner Cone 13. The Internal Taper Lock 4 serves both as an air seal and locks the metal and rubber parts together. This serves to transmit tension from the device to the Inner Cone 13, and prevents the rubber and metal components from pulling apart.

The Oral Inflation Tube 5 provides a means for the user to exhale breath into the device while the device is attached to the body. Introducing air into the device balloons the skin which is the primary means of causing mechanotransduction and skin growth. The tube is of sufficient length for the user to orally breathe into the device while standing. This feature negates or reduces the need for external inflation equipment such as bellows, pumps, syringes, or squeeze bulbs. It is connected to the Metal Core 25.

The Gripper Tension Rings 6 are multiple integrated o-rings cast into the Outer Gripper 14. These rings inhibit the excessive expansion of the Outer Gripper 14 so the shaft skin is firmly captured by the Outer Gripper 14, and prevents skin slippage and subsequent air leaks.

The Finger Grab Tabs 7 provide a convenient means for the user to actuate the Outer Gripper 14 for the purpose of placing or removing the Outer Gripper 14 over the penile shaft skin.

The Serrated Gripper Surfaces 8 are circular grooves cast on both the Inner Cone 13 and Outer Gripper 14. These grooves serve to grip into the penile shaft skin to prevent slippage and air loss when using the device.

The Double Angle Taper Cone 9 allows the rubber Inner Cone 13 and the Outer Gripper 14 to conform to the shape of the glans penis. This shape can be in the form of two angles, multiple angles, or a continuous radius so as to conform to the glans. The Inner Cone 13 and the Outer Gripper 14 provide a means to grasp the penile shaft skin.

The Compression Ferrule 10 (FIG. 2) is a stainless-steel ring which is mechanically crimped over silicone rubber to additionally lock the rubber surfaces to the metal components and prevent air leaks. It is connected to the Metal Core 25.

The Locking Collar 11 is a stainless-steel component that locks the Outer Gripper 14 in proper position. This prevents the Outer Gripper 14 from moving and thus losing its grip from penile shaft skin.

The Integrated Check Valve 12 is a component that permits the one-way flow of air into the device. The valve prevents air pressure from escaping the system. The air trapped by the valve keeps the folded penile shaft skin pressurized and ballooned. It is connected to the Metal Core 25.

The Outer Gripper 14 retains the penile shaft skin over the exterior of the Inner Cone 13. It is connected to the Metal Core 25.

The Inner Cone 13 centers the glans penis in the device and allows the penile shaft skin to be placed over the exterior of the Inner Cone 13 and permit the Outer Gripper 14 to hold the skin in position.

Figure 2:
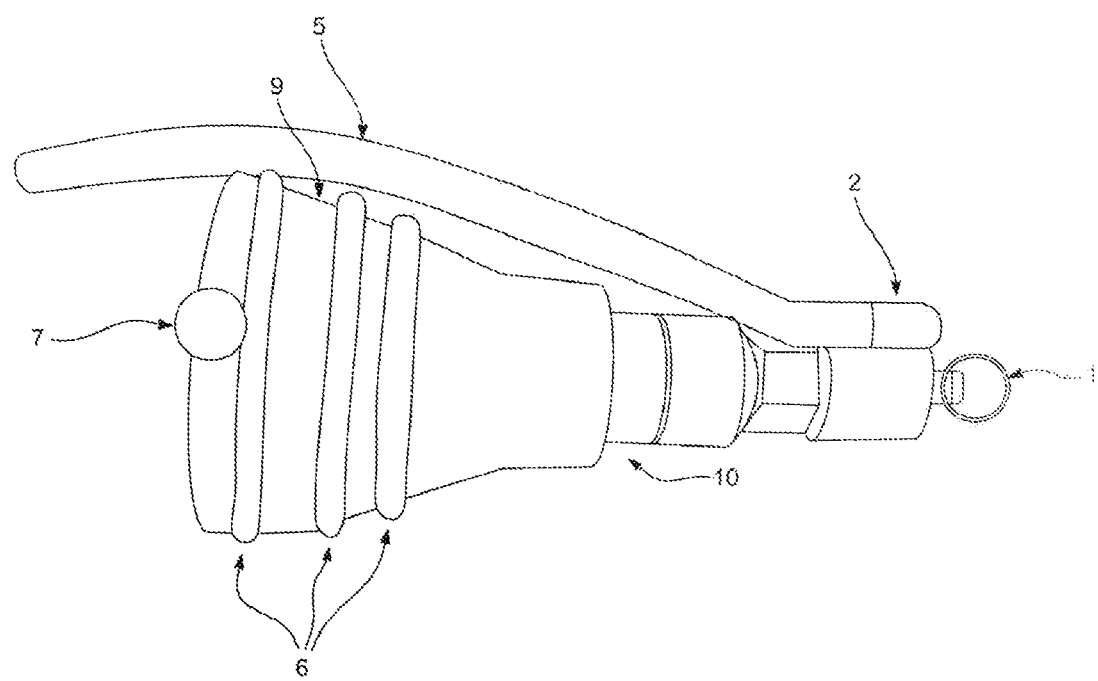
FIG. 2 is a side view of an embodiment of this invention.

FIG. 2 shows a side view of an embodiment of this invention, which comprises a Split Ring Weight Attachment Point 1, a Reversed Air Input 2, an Oral Inflation Tube 5, Gripper Tension Rings 6, Finger Grab Tabs 7, a Double Angle Taper Cone 9, a Compression Ferrule 10, and a metal core through which these components are connected, embodiments of which are each described above.

Figure 3:
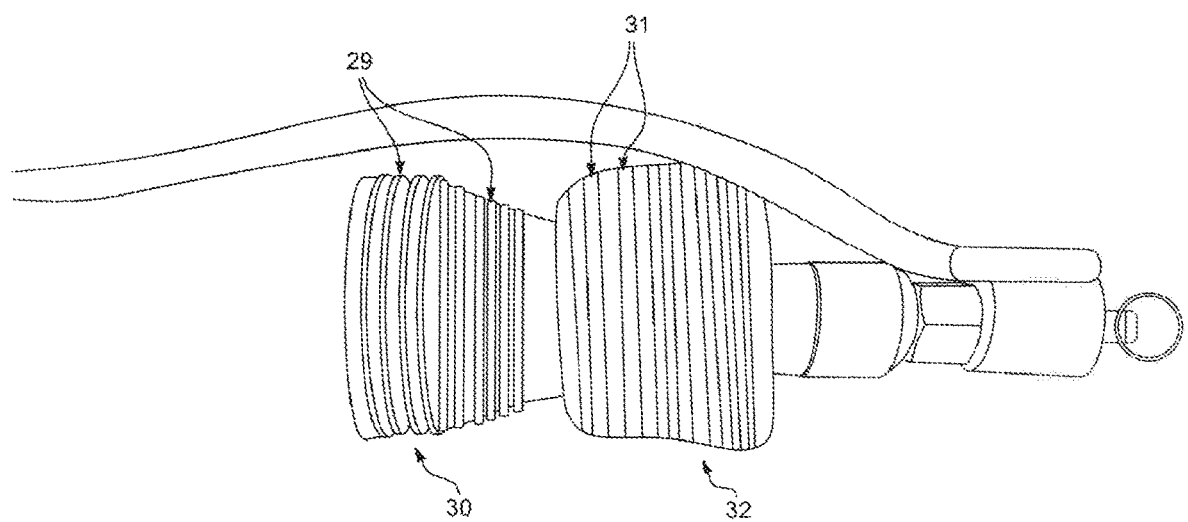
FIG. 3 is a side view of an embodiment of this invention.

FIG. 3 shows a side view of an embodiment of this invention with an inner cone and outer cone, wherein the outer cone is pulled back and not extended over the inner cone. This figure shows the Double Angle Inner Cone 29, a Grooved Inside Gripper Surface 30, a Double Angle Outer Cone 31, and a Grooved Outside Gripper Surface 32, among other components.

Example 2

In this example, methods of using the devices of Example 1 are described further. A method for penis foreskin reconstruction of this invention may comprise placing a device on the penis of the user using an outer gripper with one or more gripper tabs. The device may comprise the outer gripper, an inner cone, an oral inflation tube, and a split ring weight attachment point. The outer gripper (along with other components) forms an air-tight seal around the penis.

The method may also comprise applying air pressure to penile shaft skin so that it is held by the inner cone and the outer gripper comfortably and without slipping.

The method may also comprise adding additional tension to the device by hanging weights on the split ring weight attachment point.

Example 3

In this example, methods of using the devices of Example 1 are also described further. A method for penis foreskin restoration and reconstruction may comprise placing a device over a penis shaft using one or more finger grab tabs connected to an outer gripper.

The method may also comprise inflating penis shaft skin and holding it firmly between an inner cone and the outer gripper. This may involve the use of a metal core connected to a reversed air input that has an oral inflation tube connected to it to accept the air and raise the pressure. It may also include that each of the inner cone and the outer gripper has one or more serrated gripper surfaces integrated onto it to maintain the penis shaft skin in place. It may also include the outer gripper having one or more gripper tension rings integrated onto it to prevent excessive expansion of the outer gripper during the inflating.

The method may also comprise maintaining air pressure against the penis shaft skin. This may involve the use of an interlock seal connected to the inner cone to stop air loss. This may also include using an internal taper lock connected to the metal core and the inner cone to stop air loss. It may also include the use of one or more serrated gripper surfaces to stop air loss. It may also include the use of a compression ferrule and an integrated check valve to stop air loss. It may also include the use of one or more gripper tension rings integrated onto the outer gripper to stop it from excessively expanding after air pressure is added.

This method may also comprise applying tension to penile shaft skin by using a split ring weight attachment point to add weights to the device and thereby pull on the penile shaft skin that is being held firmly by the inner cone and the outer gripper.

Example 4

Figure 4:
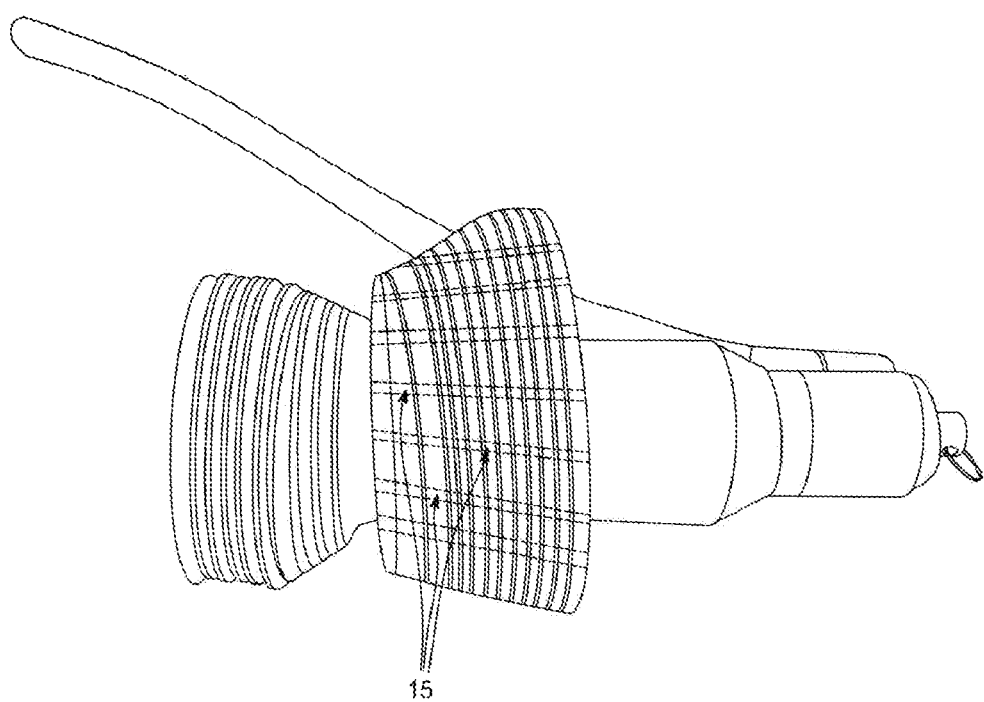
FIG. 4 is a side view of an embodiment of this invention, showing an outer gripper pulled back to show its inner surface and a plurality of circulatory relief grooves on that inner surface.

In this example, certain embodiments of this invention have a plurality of circulatory relief grooves 15 on the inner surface of the outer gripper 14. FIG. 4. These longitudinal grooves may be straight, spiral, or in other shapes and they allow blood circulation in the skin in order to reduce or prevent ischemia. Lack of blood circulation, or ischemia, in the skin may cause discomfort or painful stinging sensations. An uncomfortable restoration experience may cause the user to prematurely stop the restoration process. The circulatory relief grooves 15 may promote blood circulation and therefore provide a more comfortable user experience. The circulatory relief grooves 15 may also permit the outer gripper 14 to more freely expand to conform to the glans penis and the skin surface with less tension.

Example 5

Figure 5:
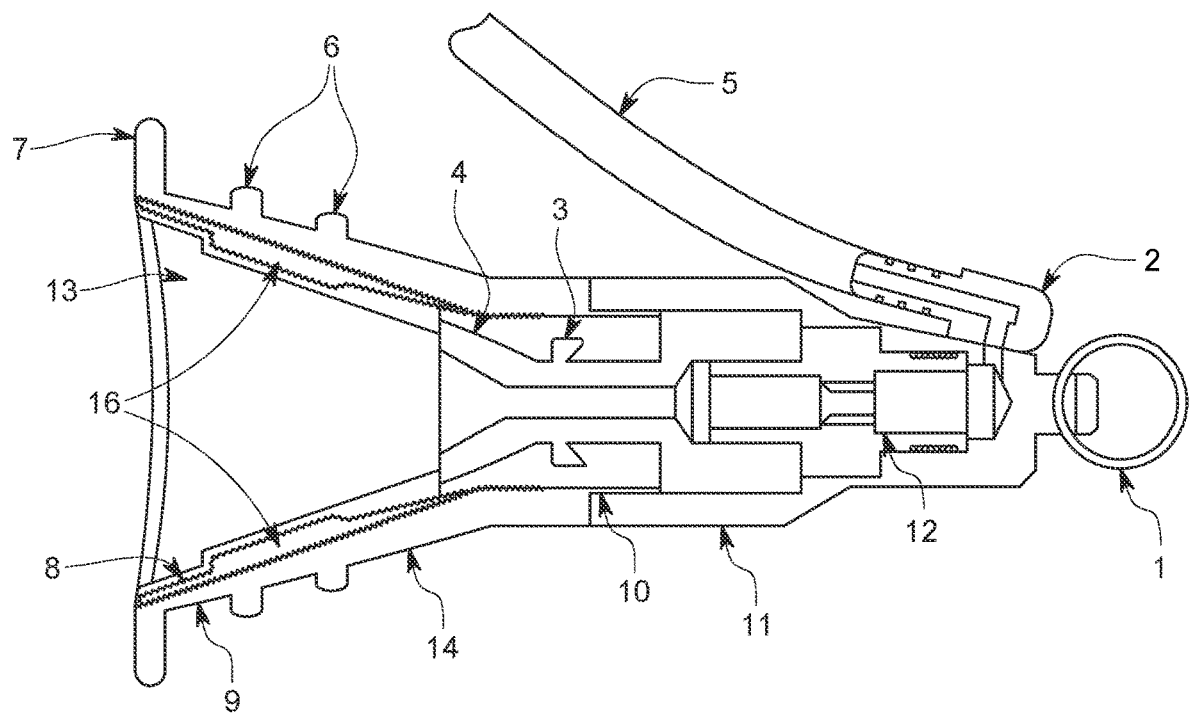
FIG. 5 is a schematic of a cross-section of a side view of an embodiment of this invention, showing a skin fold relief groove on the outer surface of an inner cone.

In this example, certain embodiments of this invention have a skin fold relief groove 16. FIG. 5. The skin fold relief groove 16 is a transverse circular groove on the outer surface of the inner cone 13. The leading edge of the folded skin, captured between the inner cone 13 and the outer gripper 14 is susceptible to possible compression, pinching and lack of blood circulation. This can become quite painful for the user as lack of circulation causes ischemia, and excessive compression can pinch this sensitive skin. Within a short period of time a user may need to remove the device due to discomfort, which could defeat the foreskin restoration process. The skin fold relief groove 16 may provide relief for this sensitive area. The leading edge of skin can retreat inside the recess to avoid being pinched and ischemic.

OTHER EMBODIMENTS

Although the present invention has been described with reference to teaching, examples and preferred embodiments, one skilled in the art can easily ascertain its essential characteristics, and without departing from the spirit and scope thereof can make various changes and modifications of the invention to adapt it to various usages and conditions. Those skilled in the art will recognize or be able to ascertain using no more than routine experimentation, many equivalents to the specific embodiments of the invention described herein. Such equivalents are encompassed by the scope of the present invention.

What is claimed is:

1. A device for penis foreskin restoration comprising:
   (a) an outer gripper with one or more outer gripper tabs configured for grasping with a hand to place the device on a penis of a user, the outer gripper covering an inner cone, wherein the outer gripper is configured to form an air-tight seal around the penis wherein the inner cone that along with the outer gripper is configured to hold penis shaft skin comfortably and without slipping;
   (b) a reversed air input connected to an oral inflation tube for blowing air into the device to add air pressure that is applied to the penis shaft skin to hold it in place and add tension;
   (c) a split ring weight attachment point on a distal end of the device that is capable of accepting weights to add tension to the penis shaft skin; and (d) a metal core that is connected to the outer gripper, the inner cone, the reversed air input, and the split ring weight attachment point.

2. The device of claim 1, wherein the outer gripper further comprises a plurality of circulatory relief grooves on its inner surface.

3. The device of claim 1, wherein the inner cone further comprises a skin fold relief groove on its outer surface.

4. A method for penis foreskin restoration comprising:
(a) placing a device on a penis of a user, the device comprising an outer gripper with one or more outer gripper tabs, an inner cone, a reversed air input connected to an oral inflation tube, and a split ring weight attachment point, wherein the outer gripper, the inner cone, the reversed air input, and the split ring weight attachment point each are connected to a metal core;
(b) applying air pressure to penile shaft skin through the oral inflation tube so that the penile shaft skin is held by the inner cone and the outer gripper comfortably and without slipping; and
(c) adding additional tension to the device by hanging weights on the split ring weight attachment point.

5. The method of claim 4, wherein the outer gripper further comprises a plurality of circulatory relief grooves on its inner surface.

6. The method of claim 4, wherein the inner cone further comprises a skin fold relief groove on its outer surface.

7. A device for penis foreskin reconstruction comprising:
(a) a metal core;
(b) a split ring weight attachment point connected to the metal core, the split ring weight attachment point capable of being used for applying weights to the distal end of the device and thereby adding tension to penis shaft skin;
(c) a reversed air input connected to the metal core that permits attachment of an oral inflation tube to the reversed air input, the oral inflation tube providing a way for a user to introduce air pressure into the device to inflate penis shaft skin;
(d) an inner cone connected to the metal core that along with an outer gripper is configured to hold penis shaft skin comfortably and without slipping;
(e) an interlock seal connected to the inner cone that prevents air escape from inside of the inner cone;
(f) an internal taper lock connected to the metal core and the inner cone and holding them together, the internal taper lock providing an air seal;
(g) one or more gripper tension rings integrated onto the outer gripper, the gripper tension rings inhibiting any excessive expansion of the outer gripper thereby preventing penis shaft skin slippage and air leaks;
(h) one or more finger grab tabs connected to the outer gripper to provide a grasping surface to place or remove the outer gripper over the penis shaft skin;
(i) one or more serrated gripper surfaces comprising circular grooves cast on both the inner cone and the outer gripper configured to grip penis shaft skin to prevent slippage and air loss, wherein the inner cone and the outer gripper are configured to conform to the shape of the penis with a double angle taper;
(j) a compression ferrule connected to the metal core and the inner cone and which locks them together and prevents air leaks;
(k) a locking collar that locks the outer gripper in a position configured to maintain a grip of the device on the penis shaft skin;
(l) an integrated check valve that is connected to the metal core and that restricts air pressure to one-way flow to prevent air pressure from escaping the device;
(m) wherein the outer gripper connected to the metal core is configured to retain the inner cone over the penis shaft skin and to make an air-tight seal over the penis; and
(n) wherein the inner cone is configured to center the penis in the device, and an exterior of the inner cone is configured to have the penis shaft skin placed over the exterior, permitting the outer gripper to hold the penis shaft skin in position.

8. The device of claim 7, wherein the outer gripper further comprises a plurality of circulatory relief grooves on its inner surface.

9. The device of claim 7, wherein the inner cone further comprises a skin fold relief groove on its outer surface.

10. A method for penis foreskin reconstruction comprising:
(a) placing a device over a penis shaft using one or more finger grab tabs connected to an outer gripper;
(b) inflating penis shaft skin and holding it firmly between an inner cone and the outer gripper comprising the use of
(i) a metal core connected to the inner cone, the outer gripper, and a reversed air input that has an oral inflation tube connected to it to accept air blown into it;
(ii) each of the inner cone and the outer gripper having one or more serrated gripper surfaces integrated onto it to maintain the penis shaft skin in place;
(iii) the outer gripper having one or more gripper tension rings integrated onto it to prevent excessive expansion of the outer gripper during the inflating;
(iv) a plurality of circulatory relief grooves on an inner surface of the outer gripper to reduce or prevent ischemia; and
(v) a skin fold relief groove on an outer surface of the inner cone to reduce or prevent pinching and ischemia of a leading edge of skin;
(c) maintaining air pressure against the penis shaft skin comprising the use of
(i) an interlock seal connected to the inner cone;
(ii) an internal taper lock connected to the metal core and the inner cone; (iii) the one or more serrated gripper surfaces;
(iv) a compression ferrule connected to the metal core and the inner cone and holding them together;
(v) an integrated check valve; and
(vi) the one or more gripper tension rings integrated onto the outer gripper; and
(d) applying tension to penile shaft skin by using a split ring weight attachment point to add weights to the device.

* * * * *